US012682787B1

(12) United States Patent
Boonya-ananta et al.

(10) Patent No.: US 12,682,787 B1
(45) Date of Patent: Jul. 14, 2026

(54) SYSTEMS AND METHODS FOR MONITORING BLOOD FLOW USING A DYNAMIC OPTICAL PHANTOM

(71) Applicants: Tananant Boonya-ananta, Miami, FL (US); Andres Julian Rodriguez, Miami, FL (US); Jessica Claudia Ramella-Roman, Miami, FL (US)

(72) Inventors: Tananant Boonya-ananta, Miami, FL (US); Andres Julian Rodriguez, Miami, FL (US); Jessica Claudia Ramella-Roman, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 19/222,638

(22) Filed: May 29, 2025

(51) Int. Cl.
    *G09B 23/28* (2006.01)
    *A61B 5/026* (2006.01)

(52) U.S. Cl.
    CPC .......... *G09B 23/286* (2013.01); *A61B 5/0261* (2013.01); *A61B 2560/0233* (2013.01)

(58) Field of Classification Search
    CPC ................ G09B 23/286; A61B 5/0261; A61B 2560/0233
    See application file for complete search history.

(56) References Cited

U.S. PATENT DOCUMENTS

| | | | | |
|---|---|---|---|---|
| 6,264,601 | B1 * | 7/2001 | Jassawalla .......... | A61M 60/178 |
| | | | | 600/16 |
| 8,318,414 | B2 * | 11/2012 | Dancu .................... | G09B 23/28 |
| | | | | 435/284.1 |
| 12,138,022 | B2 * | 11/2024 | Tokura ..................... | A61B 7/04 |
| 2011/0293074 | A1 * | 12/2011 | Coolens ............... | G09B 23/303 |
| | | | | 378/207 |
| 2012/0209086 | A1 * | 8/2012 | Beute ................... | A61B 5/7285 |
| | | | | 600/479 |
| 2021/0212654 | A1 * | 7/2021 | Zhao ...................... | A61B 6/541 |
| 2022/0233770 | A1 * | 7/2022 | Vezeridis .......... | A61M 25/0067 |
| 2022/0287656 | A1 * | 9/2022 | Leabman ............. | A61B 5/0261 |

* cited by examiner

*Primary Examiner* — Lee E Rodak
*Assistant Examiner* — Byung Ro Lee
(74) *Attorney, Agent, or Firm* — SALIWANCHIK, LLOYD & EISENSCHENK

(57) ABSTRACT

Systems and methods are provided for monitoring of blood flow using a dynamic phantom that incorporates optical properties and mechanical properties of the tissue surrounding an artery (e.g., the radial artery at the wrist). The phantom can include: a body with optical properties representative of surrounding skin layers; a vessel chamber with mechanical properties representative of the artery; and a pulsatile pump that cycles a blood-mimicking fluid (BMF) to maintain physiologically accurate pressure fluctuations typically seen at the artery. The phantom can be fabricated through the combination of rapid prototyping using both stereolithography (SLA) and fused deposition modeling (FDM) methods to develop mold casting to control geometric properties. Photoplethysmography (PPG) signals for different properties representing varying skin tone and obesity can be collected using a pulse oximeter device.

17 Claims, 17 Drawing Sheets

SECTION A-A
SCALE 2:1

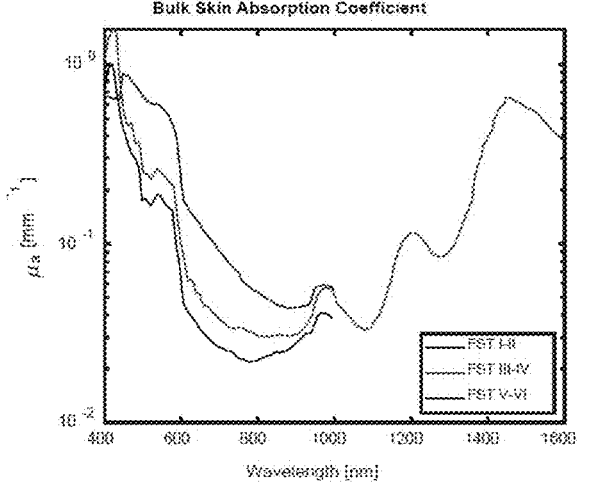
FIG. 11A                    FIG. 11B

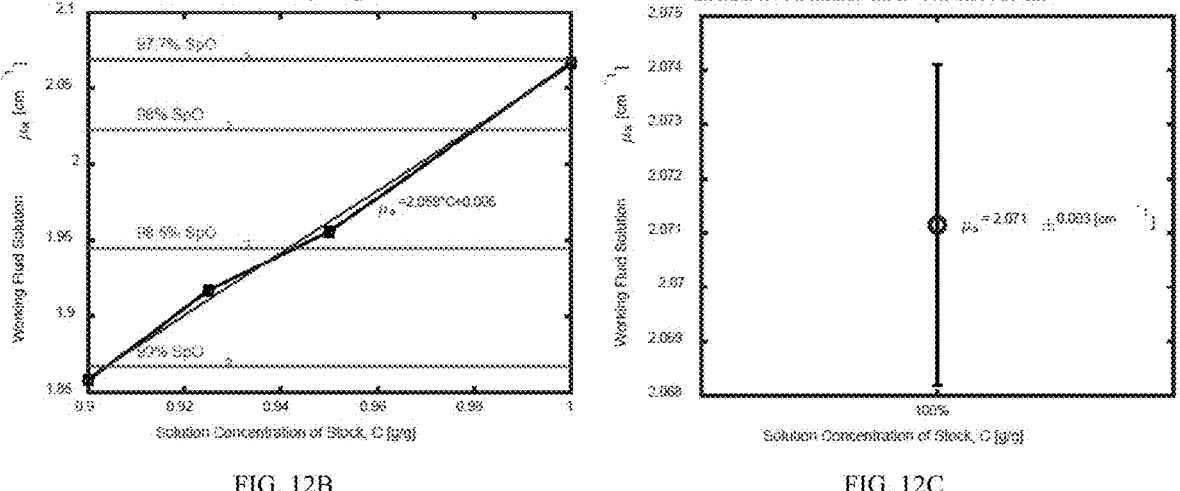
FIG. 12B                                   FIG. 12C

| Motor output voltage | 8V – 35V |
| --- | --- |
| Logic input voltage | 3V – 5.5V |
| Continuous current per phase | 1A |
| Maximum current per phase | 2A |
| Microstep resolution | full, 1/2, 1/4, 1/8 and 1/16 |

SYSTEMS AND METHODS FOR MONITORING BLOOD FLOW USING A DYNAMIC OPTICAL PHANTOM

GOVERNMENT SUPPORT

This invention was made with government support under 1648451 awarded by the National Science Foundation. The government has certain rights in the invention.

BACKGROUND

Cardiovascular disease (CVD) remains one of the leading causes of death in the United States. Currently, over 40% of the population lives with some form of cardiovascular condition, as well as varying degrees of obesity, a significant risk factor for CVD. With the ever-expanding market for health-related wearable devices, research has exposed some significant shortcomings in accurately capturing health conditions. Many of these devices utilize optical techniques, such as photoplethysmography (PPG), to probe for changes in the cardiac output waveform through the skin and surrounding tissues. However, this signal is impacted by varying skin tones and physiological changes due to obesity in a diverse population.

BRIEF SUMMARY

In view of the challenges faced in the development of optical monitoring technologies, embodiments of the subject invention provide novel and advantageous systems and methods for monitoring of blood flow using a dynamic phantom that incorporates optical properties and mechanical properties of the tissue surrounding an artery (e.g., the radial artery at the wrist). The phantom can include: a body (e.g., a silicone body) with optical properties representative of surrounding skin layers (e.g., ranging from Fitzpatrick skin type (FST) I-VI at a wavelength of 660 nanometers (nm)); a vessel chamber with mechanical properties representative of the artery (e.g., radial artery); and a pulsatile pump that cycles a blood-mimicking fluid (BMF) to maintain physiologically accurate pressure fluctuations typically seen at the artery (e.g., radial artery). The phantom can be fabricated through the combination of rapid prototyping using both stereolithography (SLA) and fused deposition modeling (FDM) methods to develop mold casting (e.g., with a silicone-based material) to control geometric properties. Photoplethysmography (PPG) signals for different properties representing varying skin tone and obesity can be collected using a pulse oximeter device.

In an embodiment, a system for monitoring blood flow can comprise: a phantom body part model (e.g., a phantom wrist model); tubing, a first portion of which is embedded in the phantom body part model; a BMF disposed in the tubing; a pressurized bulb pump flow mechanism in operable communication with the phantom body part model and configured to drive pulsatile flow of the BMF through the tubing to mimic arterial pulse behavior; a motor in operable communication with the pressurized bulb pump flow mechanism and configured to cause the pressurized bulb pump flow mechanism to compress; and an optical sensor disposed proximate to the phantom body part model and configured to optically sense properties of the BMF in the first portion of the tubing embedded in the phantom body part model during operation of the system. The system can further comprise an outlet pressure choke disposed on the tubing, and the outlet pressure choke can be configured to dynamically control and manipulate PPG waveforms sensed by the optical sensor. The system can further comprise a cam disposed on the motor and a shaft disposed between the cam and the pressurized bulb pump flow mechanism. The shaft can be in direct physical contact with the cam and the pressurized bulb pump flow mechanism. The motor can be configured to cause the cam to turn and thereby push the shaft into the pressurized bulb pump flow mechanism and compress the pressurized bulb pump flow mechanism at predetermined intervals. The tubing can comprise the first portion embedded in the phantom body part model, a second portion connecting the pressurized bulb pump flow mechanism to the first portion, a third portion connecting the first portion to a fluid reservoir, and a fourth portion connecting the fluid reservoir to the pressurized bulb pump flow mechanism. The outlet pressure choke can be disposed on, for example, the third portion of the tubing. The system can further comprise: a first one-way valve disposed on the second portion of the tubing and configured to allow the BMF to flow from the pressurized bulb pump flow mechanism to the first portion of the tubing embedded in the phantom body part model; a second one-way valve disposed on the third portion of the tubing and configured to allow the BMF to flow from the first portion of the tubing embedded in the phantom body part model to the fluid reservoir; and/or a third one-way valve disposed on the fourth portion of the tubing and configured to allow the BMF to flow from the fluid reservoir to the pressurized bulb pump flow mechanism. The BMF can comprise deionized (DI) water and India ink. The phantom body part model can comprise a material (e.g., a silicone material) configured to mimic an elasticity of skin. The phantom body part model can be three-dimensional (3D)-printed and can also comprise, for example, polylactic acid (PLA).

In another embodiment, a method for monitoring blood flow can comprise: providing a system as described in the previous paragraph, including any or all of the features described therein; operating the motor to cause the pressurized bulb pump flow mechanism to compress at predetermined intervals to mimic arterial pulse behavior; and utilizing the optical sensor to sense properties of the BMF in the first portion of the tubing embedded in the phantom body part model. The method can further comprise using the outlet pressure choke to dynamically control and manipulate PPG waveforms sensed by the optical sensor. The operating of the motor to cause the pressurized bulb pump flow mechanism to compress at predetermined intervals can comprise the BMF flowing from the pressurized bulb pump flow mechanism through the second portion to the first portion, then to the third portion, then to the fluid reservoir, then to the fourth portion, and then back to the pressurized bulb pump flow mechanism. The operating of the motor to cause the pressurized bulb pump flow mechanism to compress at predetermined intervals can comprise: the BMF flowing one way in the second portion of the tubing from the pressurized bulb pump flow mechanism to the first portion of the tubing embedded in the phantom body part model; the BMF flowing one way in the third portion of the tubing from the first portion of the tubing embedded in the phantom body part model to the fluid reservoir; and/or the BMF flowing one way in the fourth portion of the tubing from the fluid reservoir to the pressurized bulb pump flow mechanism.

BRIEF DESCRIPTION OF DRAWINGS

FIG. 1 shows certain dimensions, these are for exemplary purposes only and should not be construed as limiting.

FIG. 2 shows certain dimensions, these are for exemplary purposes only and should not be construed as limiting.

FIG. 3 shows certain dimensions, these are for exemplary purposes only and should not be construed as limiting.

FIG. 4 shows certain dimensions, these are for exemplary purposes only and should not be construed as limiting.

FIG. 5 shows certain dimensions, these are for exemplary purposes only and should not be construed as limiting.

FIG. 6 shows certain dimensions, these are for exemplary purposes only and should not be construed as limiting.

FIG. 7 shows certain dimensions, these are for exemplary purposes only and should not be construed as limiting.

FIG. 8 shows certain dimensions, these are for exemplary purposes only and should not be construed as limiting.

FIG. 9 shows certain dimensions, these are for exemplary purposes only and should not be construed as limiting.

FIG. 11A shows a plot of coefficient of static friction ($\mu_s$, in millimeters-1 ($mm^{-1}$)) versus wavelength (in nanometers (nm)) for bulk skin absorption. The curve with the highest us value at a wavelength of 600 nm is for Fitzpatrick skin type (FST) V-VI; the curve with the second-highest $\mu_s$ value at a wavelength of 600 nm is for FST III-IV; and the curve with the lowest us value at a wavelength of 600 nm is for FST I-II.

FIG. 11B shows a plot of $\mu_s$, (in $mm^{-1}$) versus wavelength (in nm) for bulk skin reduced scattering. The curve with the highest $\mu_s$ value at a wavelength of 600 nm is for FST III-IV; the curve with the second-highest $\mu_s$ value at a wavelength of 600 nm is for FST I-II; and the curve with the lowest $\mu_s$ value at a wavelength of 600 nm is for FST V-VI.

FIG. 12B shows a plot of working fluid (BMF) solution absorption (in $cm^{-1}$) at a wavelength of 660 nm versus solution concentration of stock (C; in g/g).

FIG. 12C shows an error bar for one measurement of 100% stock solution. The y-axis is working fluid solution absorption (in $cm^{-1}$), and the x-axis is solution concentration of stock (C; in g/g).

FIG. 13A shows certain dimensions, these are for exemplary purposes only and should not be construed as limiting.

FIG. 13B shows certain dimensions, these are for exemplary purposes only and should not be construed as limiting.

FIG. 14A shows a plot of output voltage amplitude (in V) versus number of samples; FIG. 14B shows a plot of output voltage amplitude (in V) versus time (in seconds (sec)); and FIG. 14C shows a plot of output voltage amplitude (in V) versus sample index.

FIGS. 17A-17C show results for HR=59.0 BPM, HR=88.5 BPM, and HR=118.0 BPM, respectively.

FIGS. 18A-18C show results for HR=59.0 BPM, HR=88.5 BPM, and HR=118.0 BPM, respectively.

DETAILED DESCRIPTION

Embodiments of the subject invention provide novel and advantageous systems and methods for monitoring of blood flow using a dynamic phantom that incorporates optical properties and mechanical properties of the tissue surrounding an artery (e.g., the radial artery at the wrist). The phantom can include: a body (e.g., a silicone body) with optical properties representative of surrounding skin layers (e.g., ranging from Fitzpatrick skin type (FST) I-VI at a wavelength of 660 nanometers (nm)); a vessel chamber with mechanical properties representative of the artery (e.g., radial artery); and a pulsatile pump that cycles a blood-mimicking fluid (BMF) to maintain physiologically accurate pressure fluctuations typically seen at the artery (e.g., radial artery). The phantom can be fabricated through the combination of rapid prototyping using both stereolithography (SLA) and fused deposition modeling (FDM) methods to develop mold casting (e.g., with a silicone-based material) to control geometric properties. Photoplethysmography (PPG) signals for different properties representing varying skin tone and obesity can be collected using a pulse oximeter device (e.g., a commercial NellCor pulse oximeter device).

Figure 10:
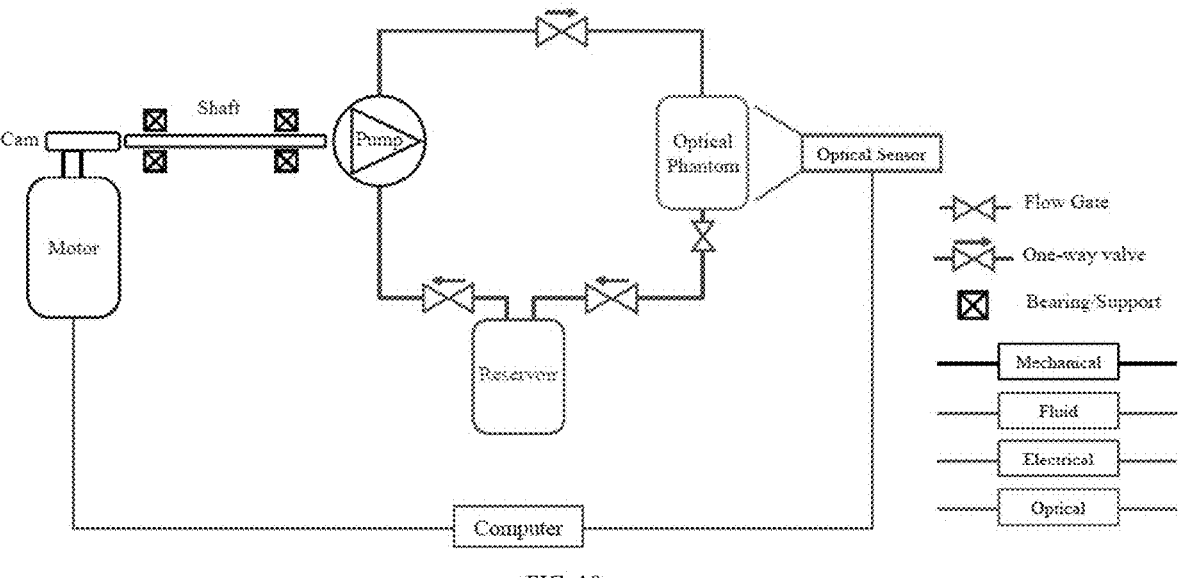
FIG. 10 shows a schematic view of a phantom, according to an embodiment of the subject invention. In order to create the mold design for the phantom, a vessel can be embedded into a three-dimensional (3D) hollow hand model. The vessel can be embedded at different depths in relation to the surface of the mold (e.g., from 1 mm deep to 3 mm deep). The mold can be, for example, 3D printed (e.g., with polylactic acid (PLA)) (e.g., on a Method X printer).

Referring to FIG. 10, the system can include a mechanical pump to replicate flow experienced in the artery (e.g., radial artery) and a phantom including the vessel chamber and human tissue mimicking media. The pump system can utilize a mechanical cam (e.g., a custom mechanical cam) and cam follower mechanism attached to a motor (e.g., a stepper motor) on a supporting structure. The cam can be designed to have a profile that mimics the wave shop of a typical PPG waveform, which is directly correlated to the fluid pressure/flow changes inside the artery (e.g., radial artery). The cam and cam follower can translate the rotational motion of the stepper motor shaft to translational motion of the cam follower, which compresses a bulb (e.g., a custom designed bulb, such as a silicone-casted custom bulb). The bulb can create a pulsatile flow fluid motion to the closed system. The flow pathway can be a one-way flow with a plurality of one-way flow valves between the critical components of the flow system. The closed looped flow can originate from a fluid reservoir, to the bulb pump, to the vessel chamber, and then back into the fluid reservoir.

The fluid can be a BMF, which may be created with optical properties matching the properties of a set percentage oxygen content of whole blood (e.g., at a wavelength of 660 nm). Fluid can be created, for example, with a combination of stock India ink and deionized (DI) water.

The phantom can be fabricated using a stereolithographic printer (e.g., from Formlabs using Elastic 50A-V1 base material). The base material can be combined with a mixture of carbon black and titanium dioxide to achieve the appropriate optical properties matching to bulk human skin. The phantom can be designed with an embedded vessel chamber whose properties and location can be altered according to appropriate effects of obesity variation desired.

Embodiments of the subject invention provide a pressurized bulb pump flow mechanism integrated with an outlet pressure choke to dynamically control and manipulate PPG waveforms. The system can mimic the physiological pulsatility of an artery (e.g., the radial artery) by creating accurate, adjustable waveforms that respond to specific variables, such as skin tone and body mass index (BMI). Through the adjustable choke mechanism, precise modulation of PPG wave characteristics can be achieved, including peak amplitude, waveform shape, and period, thus providing a versatile platform for testing wearable health devices across diverse population groups. Embodiments address a gap in the accuracy of wearable health monitoring systems, particularly for cardiovascular metrics, by allowing for reproducible testing across a controlled range of physiological conditions.

In the related art, device accuracy varies significantly across different skin tones, obesity levels, and other biological variables, leading to inconsistencies in PPG readings and limiting device reliability. Other PPG phantoms fall short in replicating the full range of arterial pulsatility and waveform manipulation necessary for testing across a diverse population. The need for a more accurate testing platform is critical to advancing health equity, particularly as wearables become more widely used in remote monitoring and telehealth applications. Embodiments of the subject invention address these limitations by providing a phantom system that can dynamically simulate physiological pulse patterns, giving a reliable testing model to improve device accuracy across diverse populations.

Embodiments of the subject invention provide comprehensive phantom-based systems configured to accurately simulate the physiological pulsatility and waveform characteristics of an artery (e.g., the radial artery) through an innovative combination of mechanical and optical components. The systems are particularly suited for testing PPG waveform behavior across varied physiological conditions, such as different skin tones and BMIs. The pressurized bulb pump flow mechanism and the adjustable outlet pressure choke, together with supplementary components, enable precise control and manipulation of the PPG waveform, facilitating testing for wearable health devices. Key components include the pressurized bulb pump flow mechanism, the outlet pressure choke, the cam mechanism for flow control, the motor and mounting platform, the BMF, the phantom wrist model and arterial embedding, and the integration of optical and mechanical properties for realistic simulation.

Pressurized Bulb Pump Flow Mechanism: The bulb pump serves as the core driver of pulsatile flow, replicating arterial pulse behavior. This mechanism allows for customization of the pulse frequency and amplitude to match physiological ranges observed in the radial artery. By generating a controlled pulsatile flow, the bulb pump supports the creation of realistic PPG waveforms that can be adjusted to represent diverse arterial behaviors.

Outlet Pressure Choke: The outlet pressure choke can be configured to fine-tune the PPG waveform's shape by regulating the flow resistance at the outlet. Adjusting the choke allows precise control over waveform attributes, including peak amplitude, primary and secondary peaks, and the amplitude decay between them. This capability provides critical flexibility in simulating waveshape PPG signal readings, enhancing the phantom's applicability in testing wearable devices across varied cardiovascular conditions.

Cam Mechanism for Flow Control: A cam mechanism driven by a stepper motor can provide additional modulation of the pulsatile flow. The cam profile can control the roller movement to compress the bulb pump at specific points, enabling manipulation of the pulsatile flow pattern. This modulation can be programmed to simulate different heart rates (e.g., 60 beats per minute (BPM) to 180 BPM) by adjusting the stepper motor speed, providing a range of waveforms for testing device sensitivity and accuracy.

Motor and Mounting Platform: A robust base platform and motor mount securely hold the motor and associated components in place. This structure ensures stable operation, minimizing vibrations and maintaining consistent output for each simulated pulse cycle. The platform's modular design enables rapid adjustments to the setup, supporting a variety of configurations for testing different device placements.

BMF: To replicate the optical properties of human blood, the system can uses a BMF comprising a precise mixture of India ink and DI water. This fluid can be configured to match the absorption spectrum of human blood, specifically targeting a coefficient at 660 nm, which is commonly used in PPG-based wearables. By simulating the optical characteristics of blood, the BMF enhances the system's realism, enabling accurate evaluation of device performance in real-world conditions.

Phantom Wrist Model and Arterial Embedding: The phantom wrist model can be fabricated with materials (e.g., silicone materials) that mimic the compliance and elasticity of human tissue. This model can include embedded tubing to represent an artery (e.g., the radial artery) at adjustable depths, allowing for controlled simulation of variations in skin tone and BMI. Depth adjustments provide a means to study how these factors impact PPG signal strength, thereby offering insights into device accuracy across populations.

Integration of Optical and Mechanical Properties for Realistic Simulation: The entire system can be configured to integrate both optical and mechanical properties to provide a comprehensive testing platform. By combining controlled pulsatile flow with a BMF and a realistic phantom wrist model, the system can ensure that the simulated PPG waveform closely resembles that of a human subject. The adjustable configuration allows for custom setups tailored to different device requirements, providing flexibility for testing both hardware and software aspects of wearable health monitors.

Figure 1:
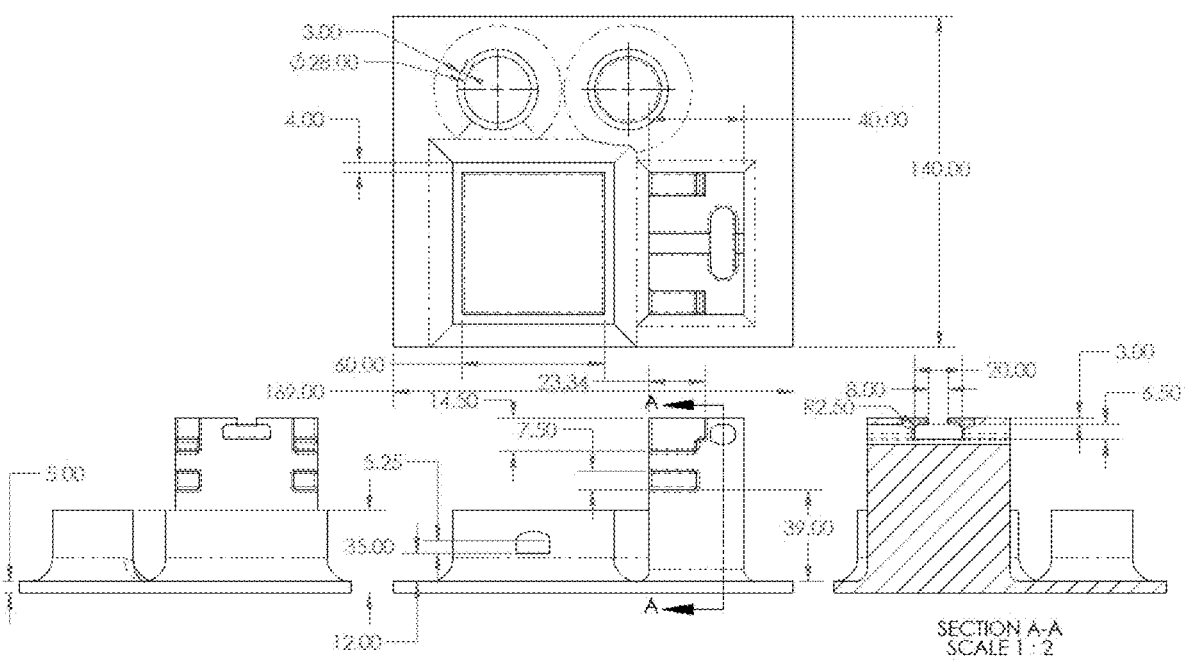
FIG. 1 shows a schematic view of a pump base plate design, according to an embodiment of the subject invention. Though

The pressurized bulb pump flow mechanism is central to the system's ability to simulate physiological pulsatile flow, generating a PPG waveform that closely resembles that of a natural radial artery. The pressurized flow is created through a combination of custom-designed components, all mounted on a secure pump base plate for stability and alignment during operation (see also FIG. 1).

Figure 2:
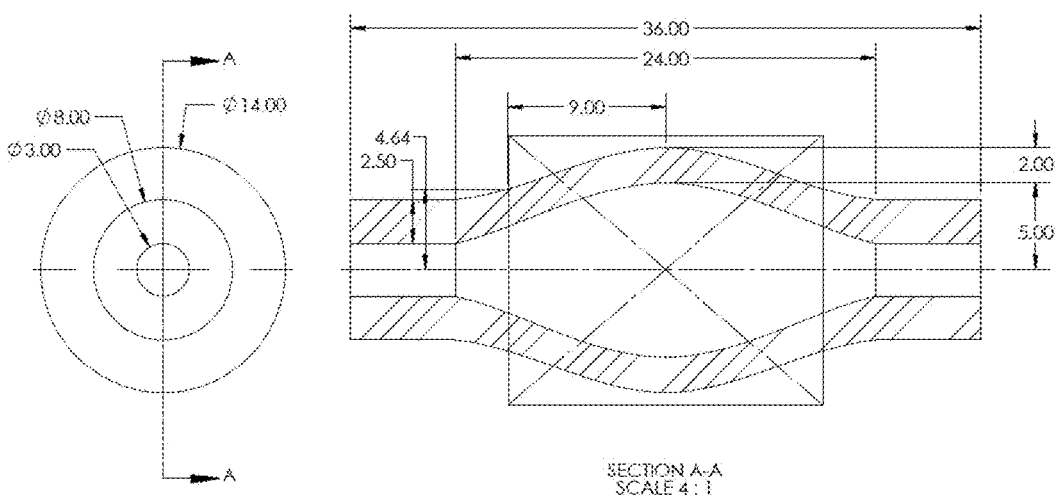
FIG. 2 shows a schematic view of a bulb configuration design, according to an embodiment of the subject invention. Though

Referring to FIG. 2, the pulsatile flow is generated by a specially designed bulb pump, which fills and discharges fluid with each motor revolution. The bulb can be engineered to output, for example, about 1100 cubic millimeters (mm³) of fluid volume with full compression, resulting in a maximum flow rate of about 5300 cubic millimeters per second (mm³/s) at a motor input frequency of 1 Hertz (Hz).

The bulb pump can be fabricated using, for example, a three-dimensional (3D)-printed shell (e.g., polylactic acid (PLA) shell) and an internal core, which define the shape and structural integrity of the bulb. To achieve the desired elasticity, the bulb can be molded from a 2-part silicone mixture with a Shore hardness of 40 A, combined with a curing agent in a 1:1 ratio. This material selection provides the necessary flexibility to withstand repetitive compression cycles, accurately mimicking the compliance of biological tissue.

Figure 3:
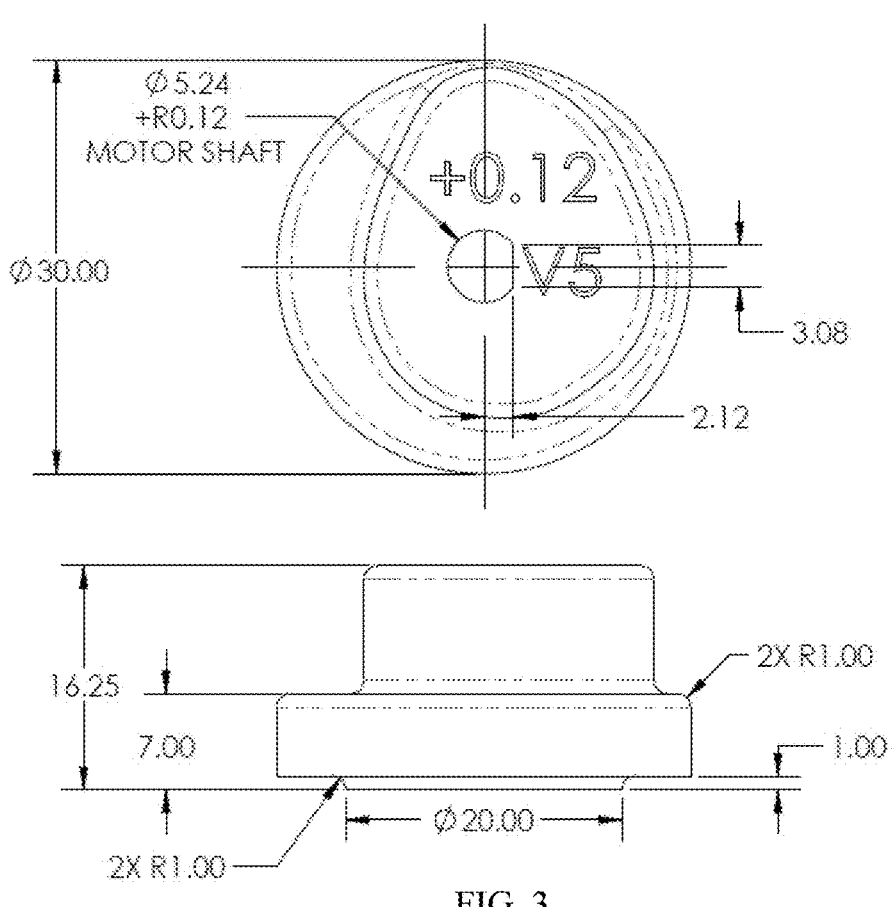
FIG. 3 shows a schematic view of a cam design, according to an embodiment of the subject invention. Though

A custom cam profile can be used to generate a characteristic two-peak waveform that mimics the systolic and diastolic peaks of a physiological pulse. The cam surface profile (see also FIG. 3) defines the timing and amplitude of each peak, with the primary peak representing the systolic phase and the secondary, smaller peak representing the diastolic phase.

Figure 4:
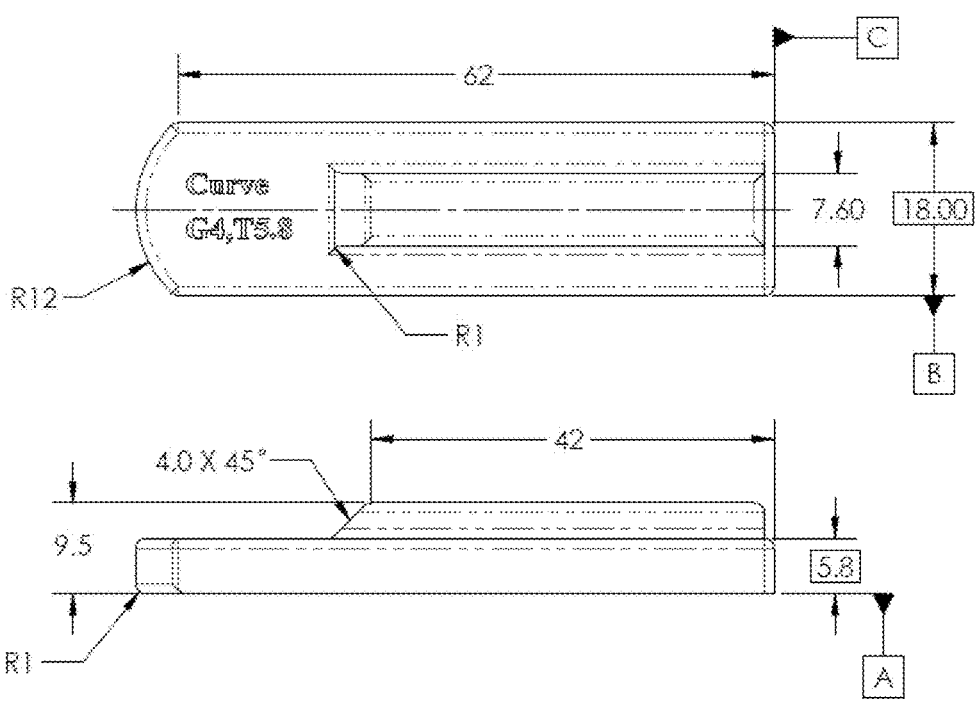
FIG. 4 shows a schematic view of a cam follower, according to an embodiment of the subject invention. Though
Figure 5:
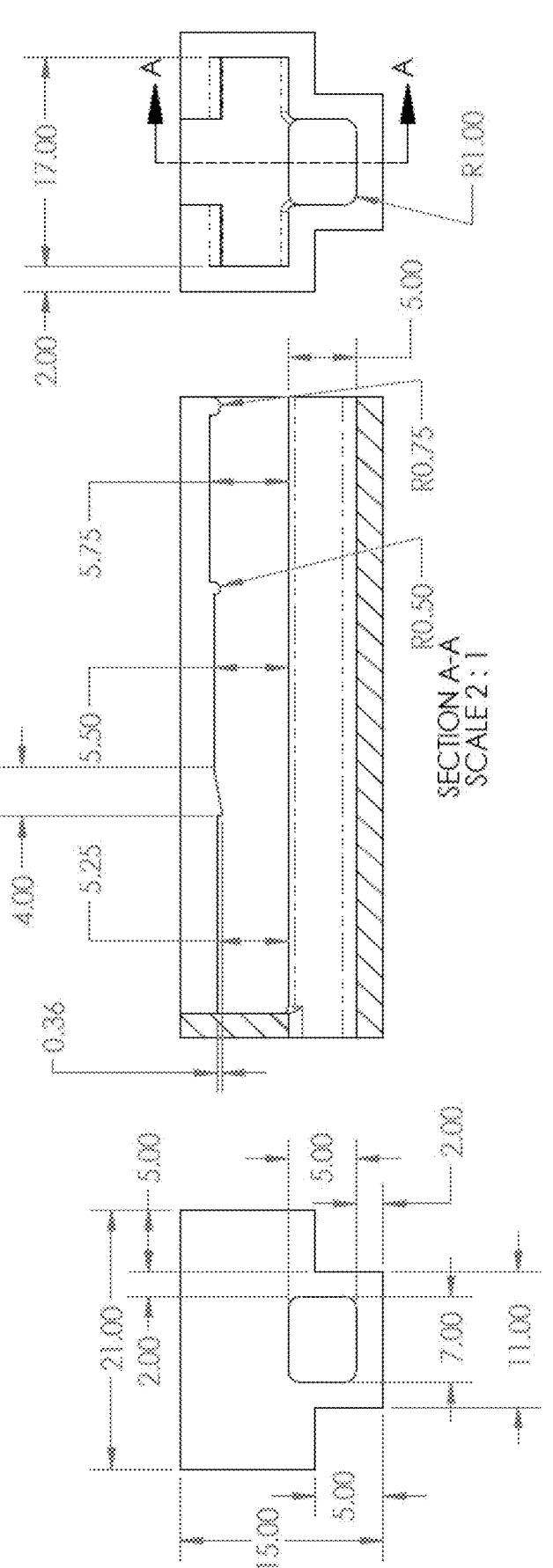
FIG. 5 shows a schematic view of an outlet choke clip stage for a silicone tubing (e.g., for 3 millimeter (mm) internal and 1 mm wall thickness), according to an embodiment of the subject invention. Though
Figure 6:
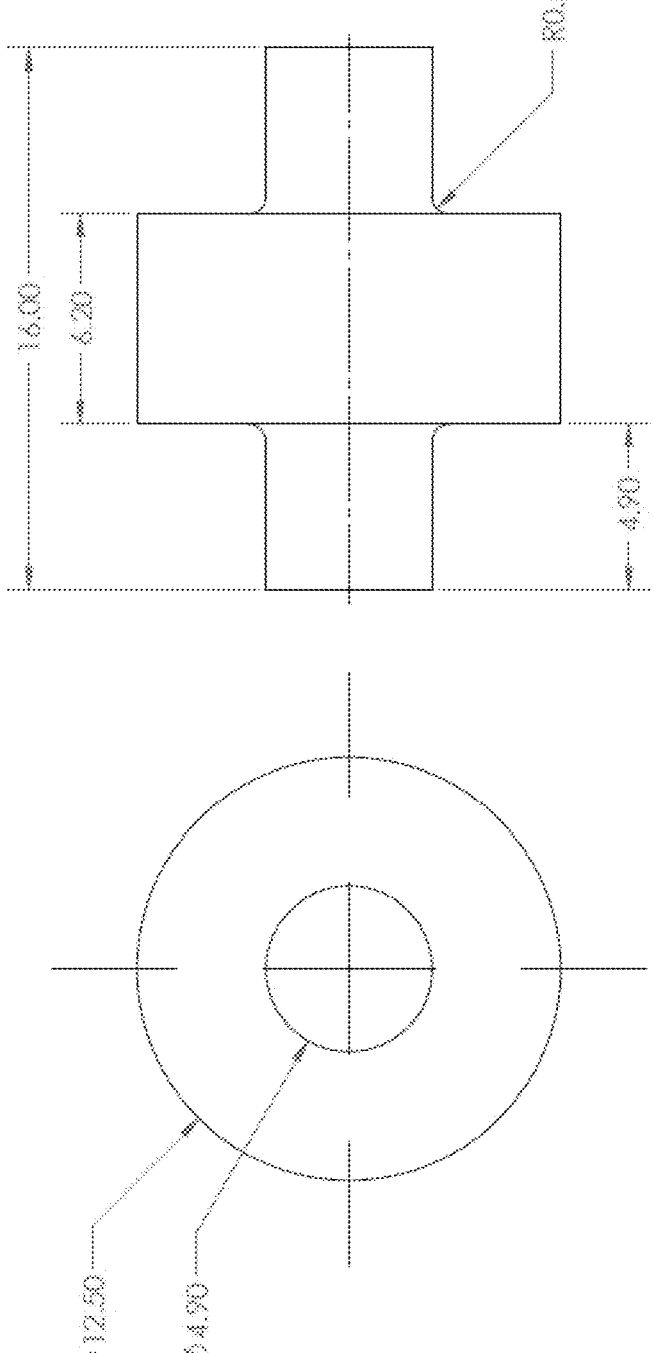
FIG. 6 shows a schematic view of an outlet choke clip roller for adjustable outlet flow restriction for the clip shown in FIG. 5, according to an embodiment of the subject invention. Though

During operation, the cam can rotate in sync with the motor, engaging with a cam follower (see also FIG. 4) that compresses the bulb at specific intervals. The interaction between the cam and cam follower can ensure a consistent flow pattern that mirrors the human pulse, allowing for adjustable waveform shapes based on the cam design and motor speed.

As the cam follower tracks the cam's surface, it compresses and releases the bulb pump in a cyclical pattern. This compression cycle discharges fluid through the outlet, simulating arterial flow. The unique cam design provides control over the volume and timing of each pulse, allowing the system to emulate different physiological conditions by adjusting parameters such as frequency and peak amplitude.

The outlet pressure choke is critical for refining the PPG waveform by controlling the resistance at the fluid outlet. By adjusting the choke mechanism, the system can modify the waveform's amplitude, shape, and duration, enabling realistic representations of various arterial conditions. This functionality is essential for testing the impact of physiological factors, such as vascular stiffness, on the PPG signal. (see also FIGS. 5, 6, 13A, and 13B).

The outlet pressure choke can apply variable restrictions to the flow as it exits the bulb pump. This flow restriction is adjustable, allowing for fine control over the pulse's characteristics, including the amplitude of the systolic and diastolic peaks and the interval between them.

The choke setting can be calibrated to influence the waveform by adding backpressure to the system, which alters the discharge rate and smooths out rapid changes in flow, resulting in a more physiologically accurate waveform.

By controlling the choke, the system can manipulate the waveform's phase relationships and peak characteristics. For example, increasing the choke restriction can extend the duration of the diastolic phase, mimicking the effects of increased vascular resistance. Decreasing the choke restriction, on the other hand, can increase peak amplitude and shorten pulse duration, representing a more open or compliant vascular state. This ability to customize the waveform ensures that the phantom system can simulate a range of physiological and pathological conditions, providing a versatile platform for testing wearable PPG devices under realistic conditions.

The choke can be integrated into the overall flow control assembly and can operate in conjunction with the bulb pump and cam mechanism. Together, these components can provide synchronized control over the pulsatile flow, allowing the system to replicate complex waveform dynamics. This setup also facilitates quick adjustments to the waveform output, enabling testing across multiple simulated physiological conditions.

Figure 19:
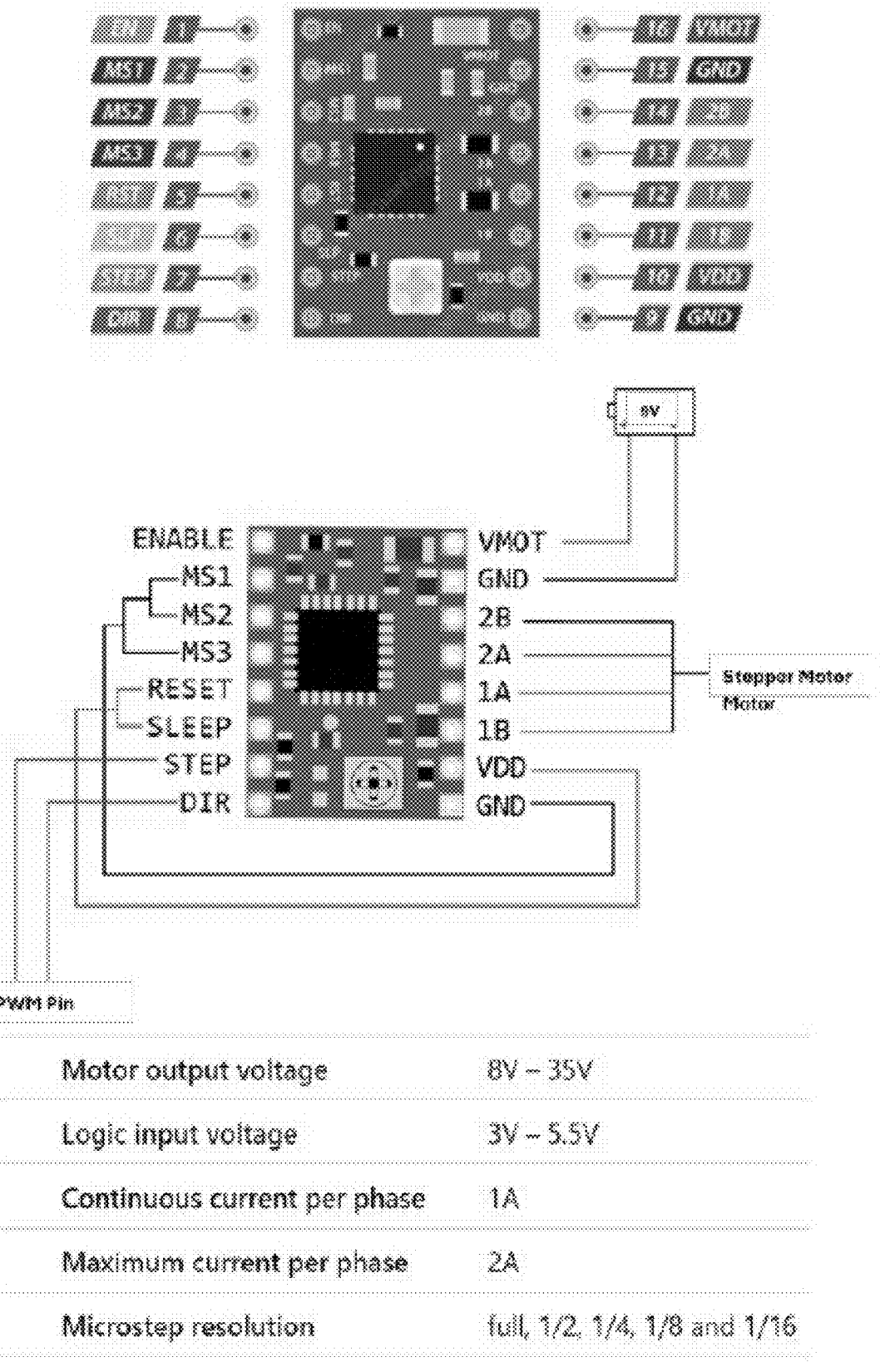
FIG. 19 shows a schematic layout of circuitry for motor controls that can be used with a phantom of an embodiment of the subject invention. It can be a stepper motor at, for example, 9 Volts (V) and 0.3 Amperes (A)-0.4 A at 60 Hertz (Hz)-120 Hz with system friction.

The cam mechanism, driven by a stepper motor (see also FIG. 19), further supports the flow control system by introducing a variable compression pattern. The roller compresses the bulb in accordance with the cam's profile, which is designed to modulate the pulsatile flow pattern dynamically.

The cam profile can be modified to produce various flow patterns, allowing the system to replicate heart rates (e.g., ranging from 1 Hz to 3 Hz) by adjusting the stepper motor's rotation speed. The cam-follower's controlled movement, guided by the cam, ensures consistent interaction with the bulb pump, maintaining the desired waveform across different flow conditions.

The stepper motor can control the rotation speed of the cam, directly influencing the frequency of the pulsatile output. This configuration allows for rapid adjustments to the simulated heart rate, making it possible to evaluate device performance under varying pulse conditions.

Figure 7:
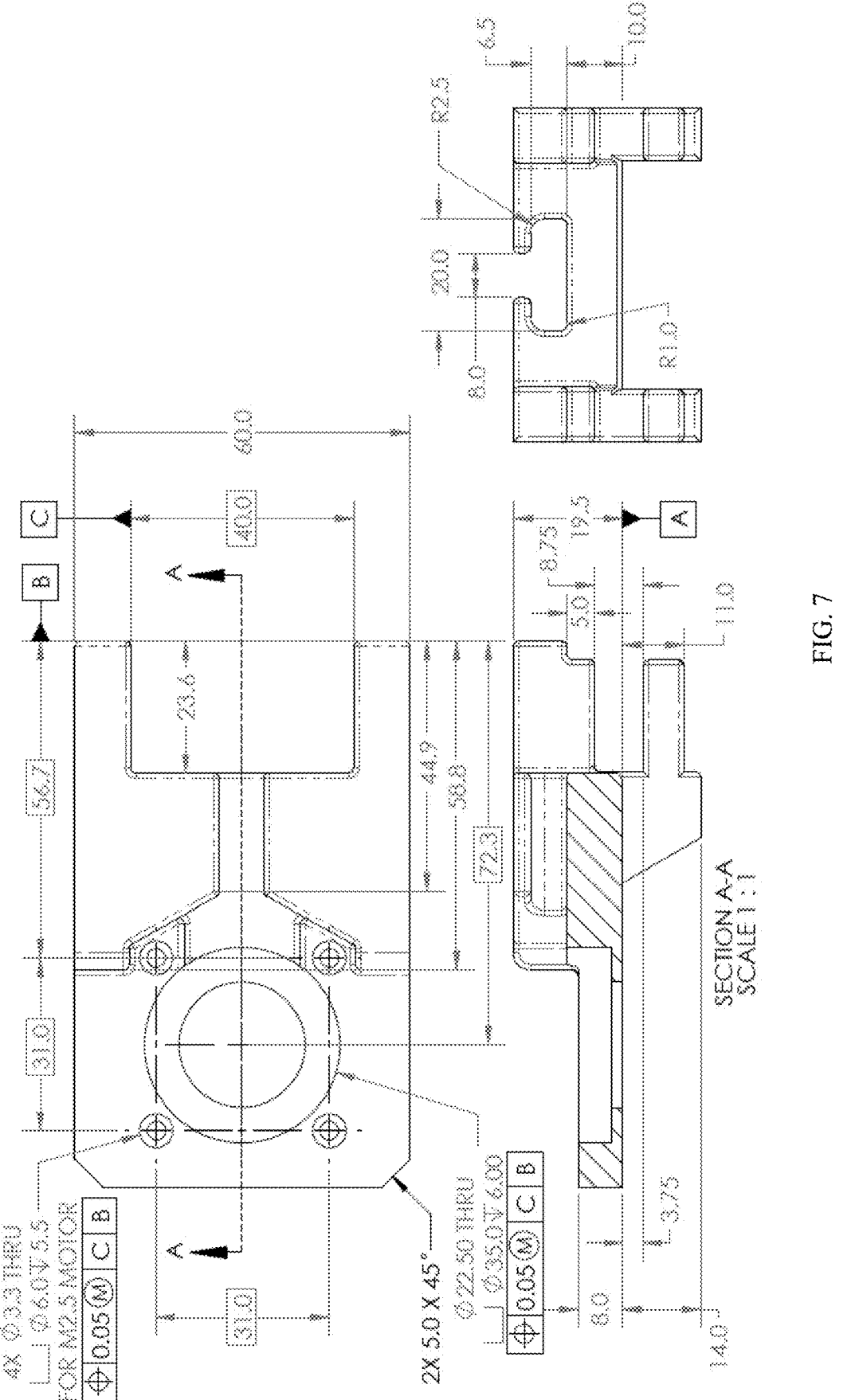
FIG. 7 shows a schematic view of a motor and a cam follower top plate for motor mounting holes, according to an embodiment of the subject invention. Though
Figure 8:
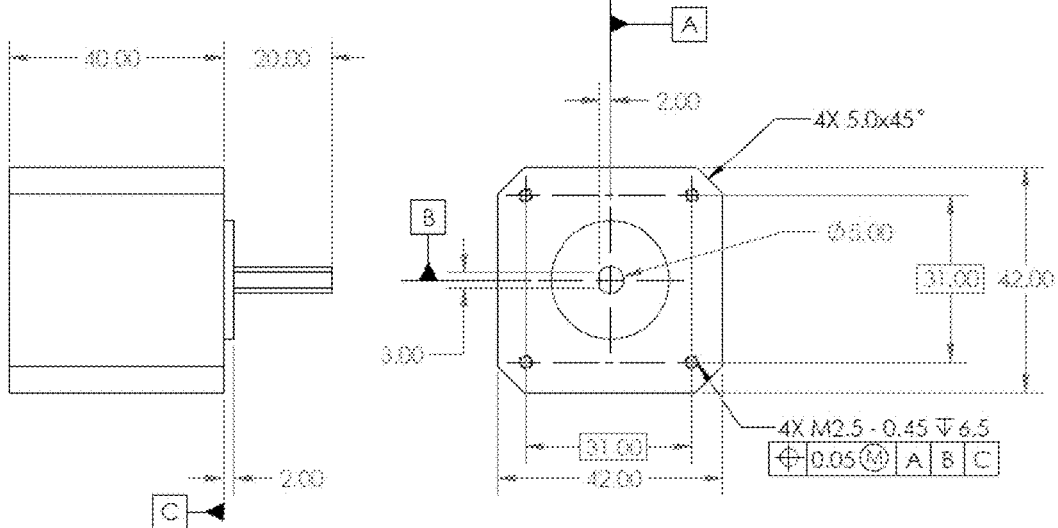
FIG. 8 shows a schematic view of a motor model with mounting holes for a current assembly, according to an embodiment of the subject invention. Though

A robust motor and base platform assembly can anchor the entire flow system, minimizing vibration and providing structural stability during operation. The platform is designed for easy component attachment and alignment, allowing users to configure the setup for specific testing needs (see also FIGS. 7 and 8).

The motor and other components can be securely mounted to the platform to prevent or inhibit mechanical shifts during operation. This stability is essential for maintaining the consistency of the output waveform, particularly at higher pulse frequencies.

The platform's modular design enables reconfiguration of components for testing different device placements or varying phantom depths, ensuring flexibility in experimental setups.

The BMF can simulate the optical characteristics of human blood, for example specifically targeting an absorption coefficient at 660 nm. This fluid is formulated with a mixture of India ink and deionized water, providing a close match to the absorption properties of real blood at common PPG wavelengths.

The BMF's absorption properties can be optimized for PPG applications, allowing for accurate reflection and transmission readings during testing. By matching the optical characteristics of blood, the BMF enables the system to provide a realistic environment for device evaluation.

The BMF can be prepared through a controlled process, where India ink concentration is calibrated to achieve a specific absorption profile. This precise composition allows the fluid to behave similarly to oxygenated and deoxygenated blood under varying lighting conditions.

Figure 9:
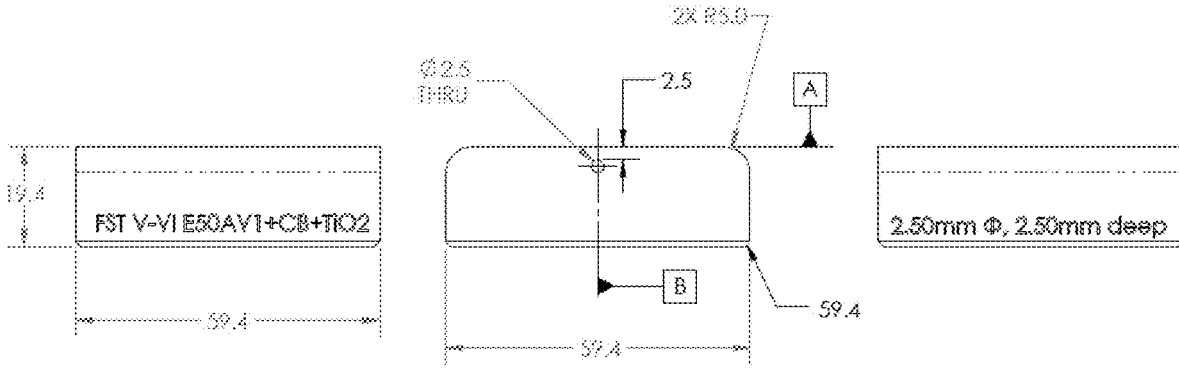
FIG. 9 shows a schematic view of an example of a silicone phantom with engraved configuration labels for vessel chamber depth and diameter, according to an embodiment of the subject invention. Though

The phantom wrist model can be fabricated from materials (e.g., silicone materials) that mimic the compliance and elasticity of human tissue. Embedded tubing can simulate an artery (e.g., the radial artery), positioned at adjustable depths to account for variations in skin tone and BMI (see also FIG. 9).

The wrist model can be cast in a material (e.g., silicone) with mechanical properties matching (or approximately matching) those of human tissue, providing a realistic environment for wearable PPG device testing. The embedded tubing can be positioned at different depths within the silicone model, allowing the phantom to mimic different levels of subcutaneous fat and skin tone.

The depth and placement of the artery within the model can be adjusted to simulate different skin tones and obesity levels, affecting the PPG signal's strength and fidelity. This feature enables device testing across a variety of demographic conditions, promoting improved accuracy in real-world applications.

The integration of these components (pressurized bulb pump, outlet pressure choke, cam mechanism, motor and base platform, blood-mimicking fluid, and phantom wrist model) creates a versatile and accurate simulation environment. By combining controlled mechanical flow with precise optical properties, the system produces a realistic PPG waveform that meets the demands of wearable health device testing.

The system can comprise an optical sensor disposed proximate to the phantom and configured to optically sense properties/characteristics of the BMF and/or BMF flow during operation of the system. The optical sensor can be in operable communication with a device (e.g., a computing device and/or a smart device) having a processor and a machine-readable medium with instructions/software stored thereon that can receive, analyze, and/or display the sensed signals and/or the sensing results.

Embodiments of the subject invention provide at least the following advantageous features.

A pulsatile phantom system with a pressurized bulb pump mechanism for generating customizable PPG waveforms, enabling realistic simulation of arterial pulse.

A method for manipulating PPG waveform features (e.g., primary and secondary peaks, amplitude, and phase) using an outlet pressure choke to regulate flow restriction.

A cam and roller-driven compression mechanism that modulates the pulsatile flow generated by the bulb pump to control heart rate simulation and waveform shape, allowing for testing at multiple physiological frequencies.

A method of generating a two-peak waveform pattern, replicating systolic and diastolic peaks in physiological pulse waveforms, achieved through specific cam profile design and adjustable motor input.

The use of a controlled outlet choke to adjust waveform attributes, offering precision in simulating various vascular conditions.

A configurable phantom allowing varied artery depths to represent skin tone and BMI effects on PPG signals.

A BMF composition, formulated to replicate human blood's optical properties at target wavelengths, providing accurate spectral absorption for wearable health device testing.

A modular base platform for securely mounting and aligning components, enabling stable operation and adjustable configuration for customized waveform generation.

A method of simulating pulse pressure by controlling both the compression force applied to the bulb pump and the outlet choke setting, allowing for consistent control over pulse amplitude and waveform characteristics.

A customizable wrist phantom model, with silicone-based arterial embedding, for adjusting subcutaneous tissue depth, supporting the study of varied skin tones and obesity levels on PPG signal fidelity.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

When ranges are used herein, combinations and subcombinations of ranges (e.g., any subrange within the disclosed range) and specific embodiments therein are intended to be explicitly included. When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to embodiments of the invention.

Example 1

A phantom was 3D printed (with PLA) and include silicone mold castings (form elastic 50A and silicon mix 30A). Absorbance was tested for FST I-II, III-IV, and V-VI. The absorber was carbon black, and the scatterer was titanium dioxide. FIGS. 11A and 11B show the results.

Example 2

Figure 12A:
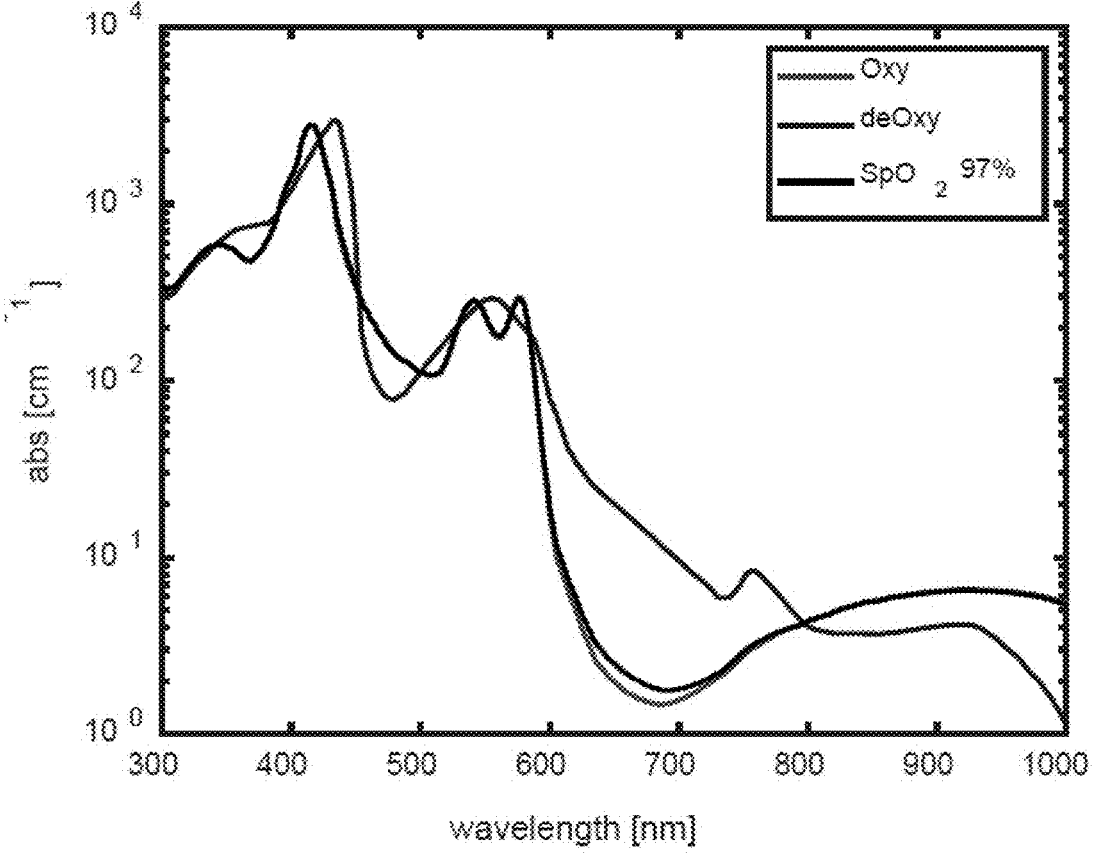
FIG. 12A shows a plot of absorption (in centimeters$^{-1}$ ($cm^{-1}$)) versus wavelength (in nm) with blood mimicking fluid (BMF). The BMF included stock solution, 465 grams (g) of deionized (DI) water, and 0.382 g of India ink (bottle stock; this included 1 fluid ounce of Higgins, and waterproof black India ink no. 44201). The curve with the highest absorption value at a wavelength of 700 nm is for deoxygenated (deoxy); the curve with the second-highest absorption value at a wavelength of 700 nm is for $SpO_2$ 97%; and The curve with the lowest absorption value at a wavelength of 700 nm is for oxygenated (oxy).
Figures 13A, 13B:
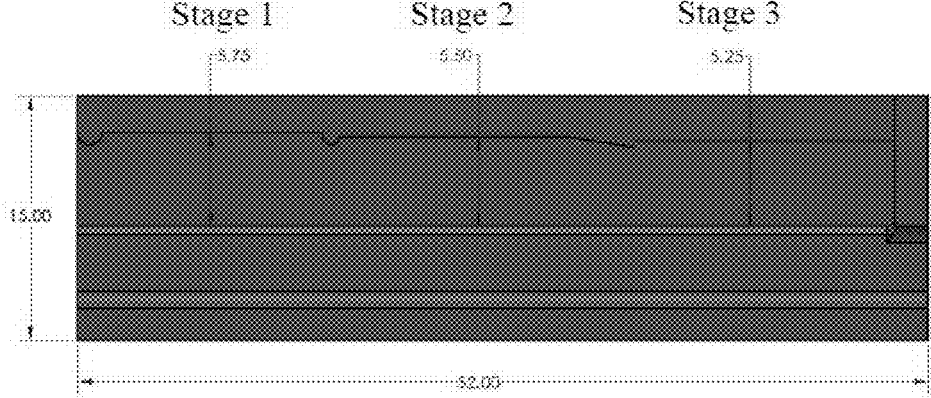
FIG. 13A shows a side view of a pressurization clip for pressure/flow choke restricting. It can include outlet pressurization via simulating physiological phenomena, pressures and flow drop to arterioles and capillaries, and loss of pulsatile signature from major artery. It can set up three-stage choking areas. Flow restriction control can be achieved through variation of clip dimensions contact with the roller. For example, the choke stages can be: stage 1-62% (or about 62%); stage 2-76% (or about 76%); and stage 3-92% (or about 92%). Though
FIG. 13B shows a cross-sectional view of the pressurization clip from FIG. 13A. Though

BMF was prepared as a stock solution with 465 grams (g) of DI water and 0.382 g of bottle stock India ink. Absorbance of the BMF was tested, with results shown in FIGS. 12A-12C.

Example 3

Figure 14A:
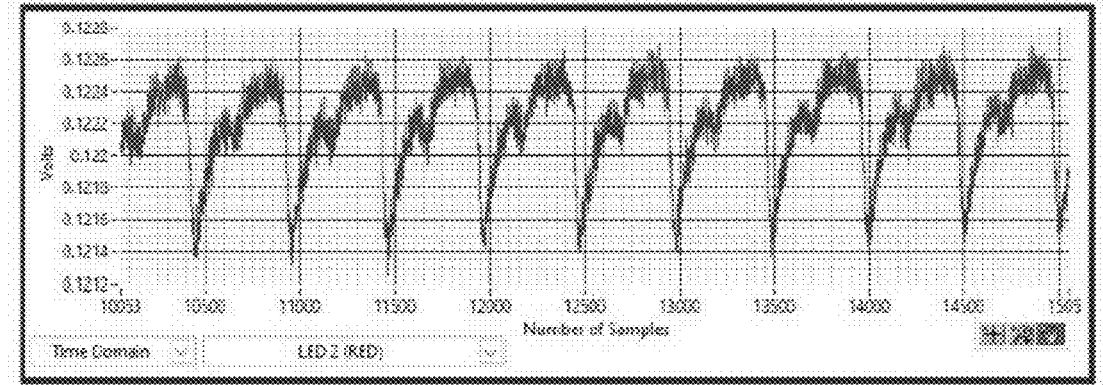
FIGS. 14A-14C show output waveforms for a phantom, obtained with a photoplethysmography (PPG) device at a wavelength of 660 nm, a physical range of 0.02%-20%, and a pulsatility index (PI) of about 1%, where PI=[(maximum pulse–minimum pulse)/mean pulse]×100%.
Figure 14B:
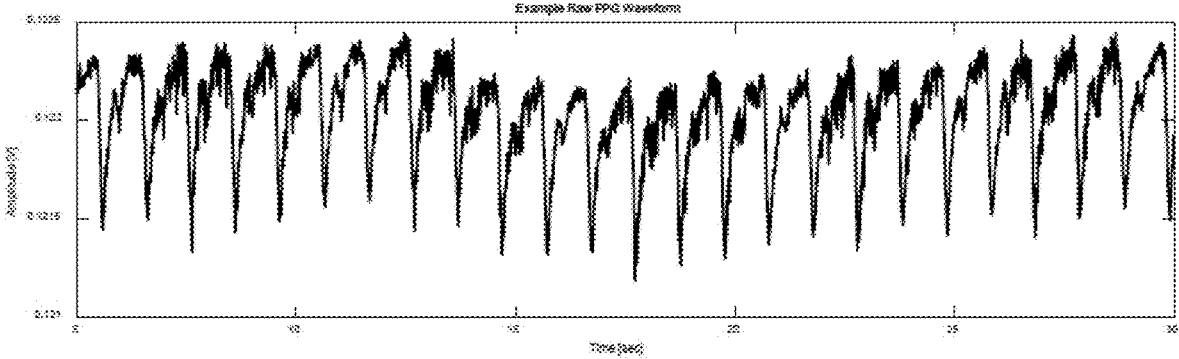
Figure 14C:
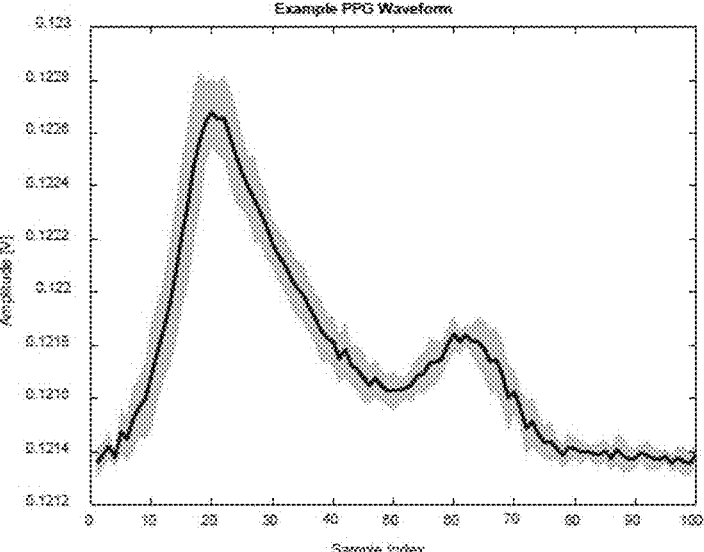
Figures 15A, 15B, 15C, 15D, 16A, 16B, 16C, 16D:
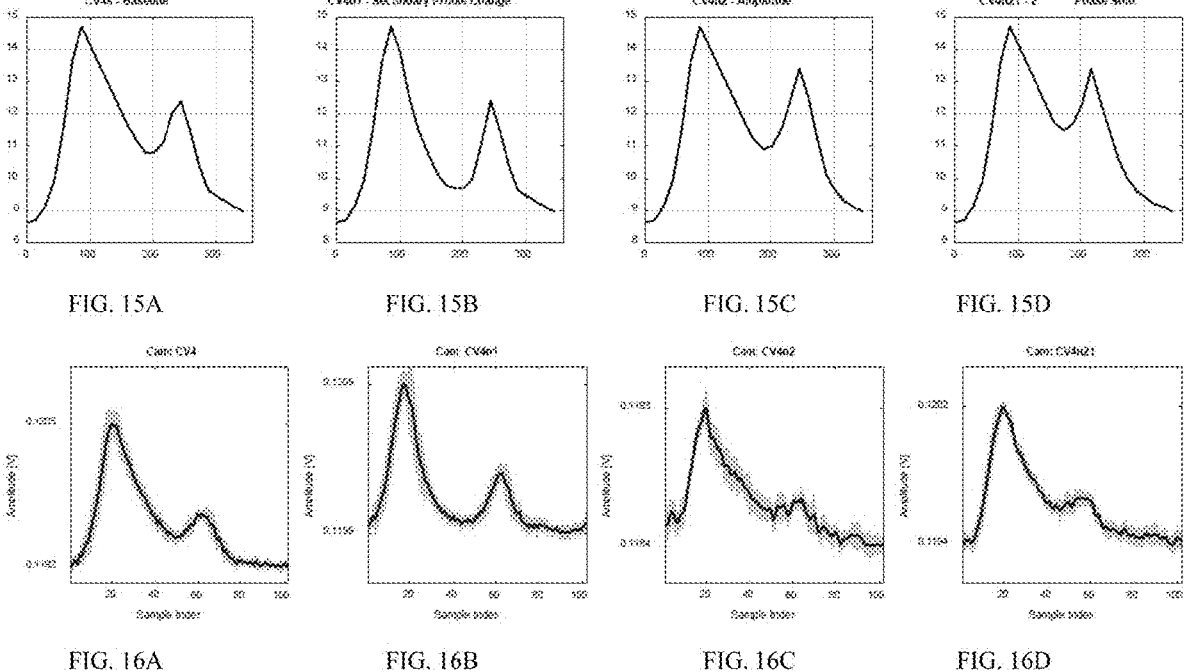
FIGS. 15A-15D show output waveforms (per sample number) with variation in cam design, all with a measured heart rate (HR) of 59 beats per minute (BPM).
FIGS. 16A-16D show output waveforms (amplitude of the voltage (in V) versus sample index) with variation in cam design, all with a measured HR of 59 BPM.
Figures 17A, 17B, 17C:
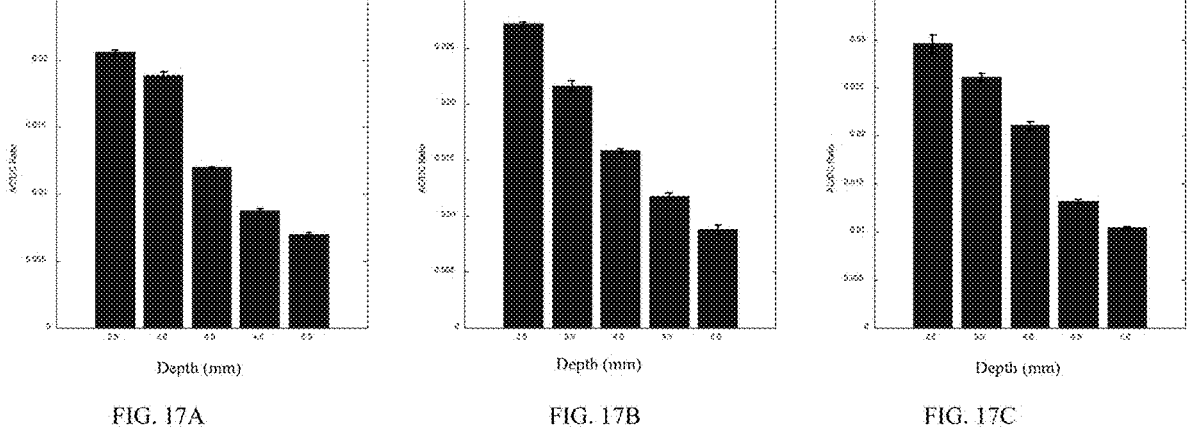
FIGS. 17A-17C show bar charts of ratio of alternating current (AC) signal to direct current (DC) signal (AC/DC ratio) versus depth (in mm). Testing parameters were: depth of 2.5 mm to 5 mm; frequency of 1 Hz, 1.5 Hz, and 2 Hz; decrease in AC/DC signal across vessel depth; baseline of 2.5 mm vessel depth; maximum of 5.0 mm vessel depth; and wavelength of 660 nm.
Figure 18A:
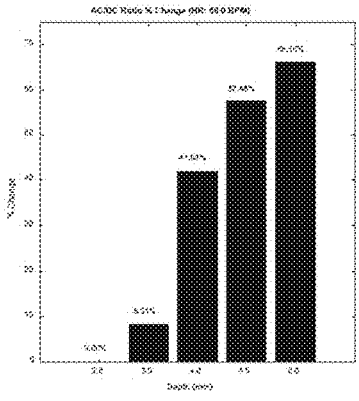
FIGS. 18A-18C show bar charts of percentage change in AC/DC ratio versus depth (in mm). Testing parameters were: depth of 2.5 mm to 5 mm; frequency of 1 Hz, 1.5 Hz, and 2 Hz; decrease in AC/DC signal across vessel depth; baseline of 2.5 mm vessel depth; maximum of 5.0 mm vessel depth; and wavelength of 660 nm.
Figure 18B:
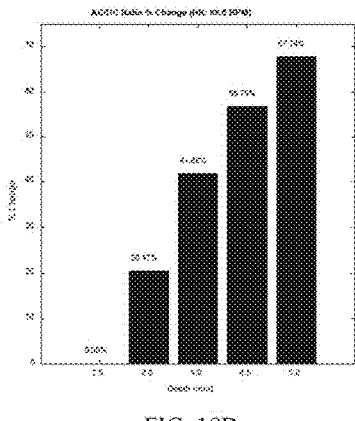
Figure 18C:
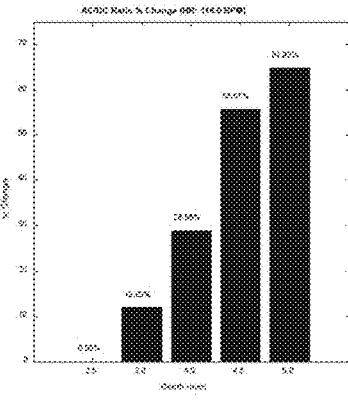

Output waveforms were obtained from the system shown in FIGS. 1-10. The results are shown in FIGS. 14A-14C. The testing parameters are listed in the brief description of FIGS. 14A-14C. The cam design was varied, and the resulting output waveforms are shown in FIGS. 15A-16D.

Next, a comparison of alternating current (AC) to direct current (DC) ratio (AC/DC ratio was performed at different skin depths and different heart rates. The results are shown in FIGS. 17A-18C. The testing parameters are listed in brief description of FIGS. 17A-17C and the brief description of FIGS. 18A-18C.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A system for monitoring blood flow, the system comprising:
   a phantom body part model that mimics compliance and elasticity of human skin;
   tubing, a first portion of which is embedded in the phantom body part model;
   a blood-mimicking fluid (BMF) disposed in the tubing;
   a pressurized bulb pump flow mechanism in operable communication with the phantom body part model and configured to drive pulsatile flow of the BMF through the tubing to mimic arterial pulse behavior;
   a motor in operable communication with the pressurized bulb pump flow mechanism and configured to cause the pressurized bulb pump flow mechanism to compress;
   an optical sensor disposed proximate to the phantom body part model and configured to optically sense photoplethysmography (PPG) waveforms of the BMF in the first portion of the tubing embedded in the phantom body part model during operation of the system; and
   an outlet pressure choke disposed on the tubing and configured to dynamically control and manipulate the PPG waveforms sensed by the optical sensor.

2. The system according to claim 1, further comprising a cam disposed on the motor and a shaft disposed between the cam and the pressurized bulb pump flow mechanism,
   the shaft being in direct physical contact with the cam and the pressurized bulb pump flow mechanism, and
   the motor being configured to cause the cam to turn and thereby push the shaft into the pressurized bulb pump flow mechanism and compress the pressurized bulb pump flow mechanism at predetermined intervals.

3. The system according to claim 1, the tubing comprising the first portion, a second portion connecting the pressurized bulb pump flow mechanism to the first portion, a third portion connecting the first portion to a fluid reservoir, and a fourth portion connecting the fluid reservoir to the pressurized bulb pump flow mechanism.

4. The system according to claim 3, further comprising a first one-way valve disposed on the second portion of the tubing and configured to allow the BMF to flow from the pressurized bulb pump flow mechanism to the first portion of the tubing embedded in the phantom body part model.

5. The system according to claim 4, further comprising:
   a second one-way valve disposed on the third portion of the tubing and configured to allow the BMF to flow from the first portion of the tubing embedded in the phantom body part model to the fluid reservoir; and
   a third one-way valve disposed on the fourth portion of the tubing and configured to allow the BMF to flow from the fluid reservoir to the pressurized bulb pump flow mechanism.

6. The system according to claim 4, the outlet pressure choke being disposed on the third portion of the tubing.

7. The system according to claim 1, the BMF comprising deionized water and India ink.

8. The system according to claim 1, the phantom body part model comprising a silicone material.

9. A method for monitoring blood flow, the method comprising:
   providing the system according to claim 1;
   operating the motor to cause the pressurized bulb pump flow mechanism to compress at predetermined intervals to mimic arterial pulse behavior;

utilizing the optical sensor to sense PPG waveforms of the BMF in the first portion of the tubing embedded in the phantom body part model; and using the outlet pressure choke to dynamically control and manipulate the PPG waveforms sensed by the optical sensor.

10. The method according to claim 9, the system further comprising a cam disposed on the motor and a shaft disposed between the cam and the pressurized bulb pump flow mechanism, the shaft being in direct physical contact with the cam and the pressurized bulb pump flow mechanism, and the motor being configured to cause the cam to turn and thereby push the shaft into the pressurized bulb pump flow mechanism and compress the pressurized bulb pump flow mechanism at predetermined intervals.

11. The method according to claim 9, the tubing comprising the first portion, a second portion connecting the pressurized bulb pump flow mechanism to the first portion, a third portion connecting the first portion to a fluid reservoir, and a fourth portion connecting the fluid reservoir to the pressurized bulb pump flow mechanism, and the operating of the motor to cause the pressurized bulb pump flow mechanism to compress at predetermined intervals comprising the BMF flowing from the pressurized bulb pump flow mechanism through the second portion to the first portion, then to the third portion, then to the fluid reservoir, then to the fourth portion, and then back to the pressurized bulb pump flow mechanism.

12. The method according to claim 11, the system further comprising a first one-way valve disposed on the second portion of the tubing, and the operating of the motor to cause the pressurized bulb pump flow mechanism to compress at predetermined intervals comprising the BMF flowing one way in the second portion of the tubing from the pressurized bulb pump flow mechanism to the first portion of the tubing embedded in the phantom body part model.

13. The method according to claim 12, the system further comprising:

a second one-way valve disposed on the third portion of the tubing; and a third one-way valve disposed on the fourth portion of the tubing, the operating of the motor to cause the pressurized bulb pump flow mechanism to compress at predetermined intervals comprising the BMF flowing one way in the third portion of the tubing from the first portion of the tubing embedded in the phantom body part model to the fluid reservoir, and the operating of the motor to cause the pressurized bulb pump flow mechanism to compress at predetermined intervals comprising the BMF flowing one way in the fourth portion of the tubing from the fluid reservoir to the pressurized bulb pump flow mechanism.

14. The method according to claim 9, the BMF comprising deionized water and India ink.

15. The method according to claim 9, the phantom body part model comprising a silicone material.

16. A system for monitoring blood flow, the system comprising:

a phantom body part model that mimics compliance and elasticity of human skin;

tubing, a first portion of which is embedded in the phantom body part model;

a blood-mimicking fluid (BMF) disposed in the tubing;

a pressurized bulb pump flow mechanism in operable communication with the phantom body part model and configured to drive pulsatile flow of the BMF through the tubing to mimic arterial pulse behavior;

a motor in operable communication with the pressurized bulb pump flow mechanism and configured to cause the pressurized bulb pump flow mechanism to compress;

a cam disposed on the motor and a shaft disposed between the cam and the pressurized bulb pump flow mechanism; and an optical sensor disposed proximate to the phantom body part model and configured to optically sense photoplethysmography (PPG) waveforms of the BMF in the first portion of the tubing embedded in the phantom body part model during operation of the system, the shaft being in direct physical contact with the cam and the pressurized bulb pump flow mechanism, the motor being configured to cause the cam to turn and thereby push the shaft into the pressurized bulb pump flow mechanism and compress the pressurized bulb pump flow mechanism at predetermined intervals, the tubing comprising the first portion, a second portion connecting the pressurized bulb pump flow mechanism to the first portion, a third portion connecting the first portion to a fluid reservoir, and a fourth portion connecting the fluid reservoir to the pressurized bulb pump flow mechanism, and the system further comprising:

an outlet pressure choke disposed on the third portion of the tubing, the outlet pressure choke being configured to dynamically control and manipulate the PPG waveforms sensed by the optical sensor;

a first one-way valve disposed on the second portion of the tubing and configured to allow the BMF to flow from the pressurized bulb pump flow mechanism to the first portion of the tubing embedded in the phantom body part model;

a second one-way valve disposed on the third portion of the tubing and configured to allow the BMF to flow from the first portion of the tubing embedded in the phantom body part model to the fluid reservoir; and a third one-way valve disposed on the fourth portion of the tubing and configured to allow the BMF to flow from the fluid reservoir to the pressurized bulb pump flow mechanism.

17. The system according to claim 16, the BMF comprising deionized water and India ink, the phantom body part model being a phantom wrist model, and the material of the phantom body part model being a silicone material.

* * * * *